United States Patent [19]

Tucker

[11] Patent Number: 4,791,707
[45] Date of Patent: Dec. 20, 1988

[54] CLIP APPLICATOR, SPREADABLE CLIPS AND METHOD FOR APPLYING THE CLIPS

[76] Inventor: Wilson H. Tucker, Box 265, RD-1,, Mystic, Conn. 06355

[21] Appl. No.: 900,385

[22] Filed: Aug. 26, 1986

[51] Int. Cl.4 ............................................. A61B 17/00
[52] U.S. Cl. .............................. 227/19; 227/DIG. 1; 227/120; 29/235; 29/243.56
[58] Field of Search .................... 227/19, 120, DIG. 1; 29/243.56, 235, 745

[56] References Cited

U.S. PATENT DOCUMENTS

| | | | |
|---|---|---|---|
| 2,764,160 | 9/1956 | Alexander et al. | 29/235 X |
| 3,098,232 | 7/1963 | Brown | 227/DIG. 1 |
| 4,034,450 | 7/1977 | Carlomagno et al. | 29/745 X |
| 4,261,098 | 4/1981 | Lincoln | 29/243.56 |
| 4,353,157 | 10/1982 | Sato | 29/243.56 |
| 4,432,124 | 2/1984 | Breuers | 29/235 |
| 4,522,207 | 6/1985 | Klieman et al. | 227/DIG. 1 |
| 4,581,805 | 4/1986 | Wrobel et al. | 29/243.56 X |
| 4,637,395 | 1/1987 | Caspar et al. | 227/DIG. 1 |

FOREIGN PATENT DOCUMENTS

690435  4/1940  Fed. Rep. of Germany .

Primary Examiner—Paul A. Bell

[57] ABSTRACT

A manual applicator for the application of spreadable surgical clips comprises a clip magazine which releasably retains therein a plurality of spreadable clips, and a spreader mounted at the discharge end of the clip magazine by a support, e.g., a rail. The spreader has an inlet section disposed adjacent to the discharge end of the magazine, and at its opposite end a discharge tip which is wider in the clip-spreading direction than its inlet section. The spreadable clips, which are resilient so that they can be spread-apart and will close upon release of the spreading force, include an opening in the rear or bight portion enabling the clip to pass over the spreader. The clips may also have a radial slot, enabling them to pass over the rail member, when the latter is not a cantilevered rail member on which the clips are threaded. The spreader has a wedge-shaped profile so that dislodgement of the spreadable clips from the magazine onto the spreader spreads the dislodged clip for ejection of the spread clip over the discharge tip of the spreader and onto the tissue to be clipped or clamped.

In the method of use, the surgeon or operator slides the clips, one at a time, onto the spreader to spread the clips on the spreader, and then discharges the spread clips over the discharge tip and onto tissue to be engaged by the clip.

23 Claims, 3 Drawing Sheets

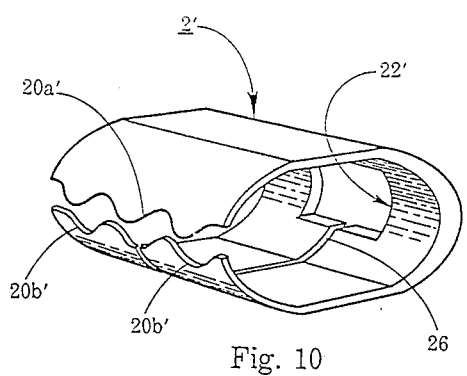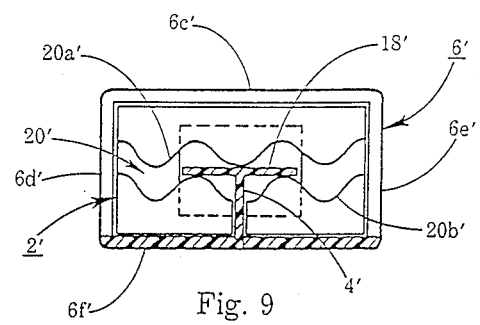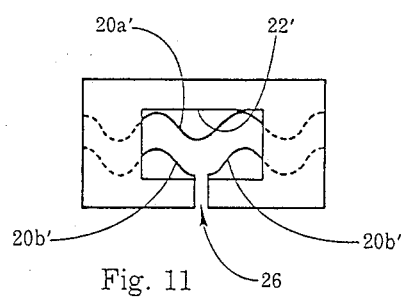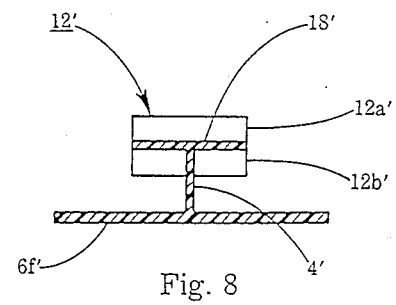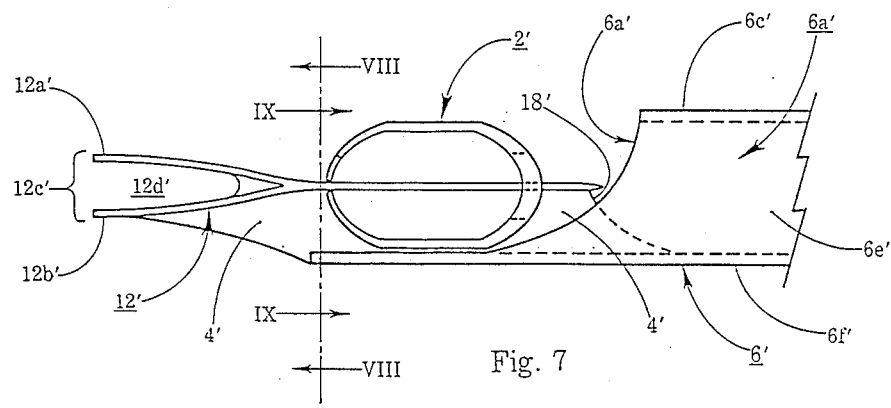

CLIP APPLICATOR, SPREADABLE CLIPS AND METHOD FOR APPLYING THE CLIPS

BACKGROUND OF THE INVENTION

1. Field Of The Invention

The present invention pertains to a novel and improved applicator for applying spreadable clips, to spreadable clips adapted for use with the applicator, especially spreadable surgical clips such as hemostatic clips, wound clasps and the like, and to a method of applying such clips.

2. Description Of Related Art

Spreadable clips, especially spreadable surgical clips as hemostatic clips and applicators for applying them to a wound or incision, are well known in the art. For example, U.S. Pat. No. 4,217,902 issued Aug. 19, 1980 to Alfred L. March, discloses a hemostatic clip for clamping together the edges of an incision or wound and an applicator for such clips. The clips comprise short segments of a longitudinally split cylinder having a longitudinally extending depression which is generally U-shaped in profile and extends opposite and parallel to the longitudinally extending split. Means are provided on the clip to cooperate with a pliers-like applicator tool which engages a single clip to spread it apart for application to the wound or incision so that, upon release of the pliers, the resiliency of the clips causes it to close to clampingly engage the wound or incision. Only one clip at a time can be loaded onto the applicator.

U.S. Pat. No. 3,098,232 issued July 22, 1963 to A. M. Brown and U.S. Pat. No. 4,372,316 issued Feb. 8, 1983 to J. W. Blake et al show surgical clip applicators designed to apply clips which are generally U-shaped in profile and which are crimpable by the applicator to crimp them from their open position to a closed position in order to seal the edges of a wound or incision.

U.S. Pat. No. 4,522,207 issued June 11, 1985 to C. H. Klieman et al shows a forceps-like device utilizing a clip magazine which is also designed to crimp to a closed position normally open, U-shaped clips.

SUMMARY OF THE INVENTION

In accordance with the present invention, there is provided a manual applicator for the application of spreadable surgical clips. The applicator comprises a clip magazine dimensioned and configured to releasably retain therein a plurality of spreadable clips and having a clip discharge end, and a spreader. The spreader is mounted on the clip magazine by a support member and has an inlet section disposed adjacent to the clip discharge end of the magazine and a discharge tip which is wider in the clip-spreading direction than its inlet section, so that the spreader has a wedge-shaped profile. The spreader and its support member are dimensioned and configured to permit sliding movement thereover of spreadable clips from the clip magazine. In this way, dislodgement of the spreadable clips from the clip magazine onto the spreader spreads the dislodged clip for ejection of the spread clip over the discharge tip of the spreader.

One aspect of the invention provides the support member in the form of a rail member, which may be cantilevered and carry the spreader on its free end, or which may comprise, for example, a vertically disposed, web-like rail member supporting the spreader. The rail member may extend parallel to or along the longitudinal axis of the applicator and a plurality of spreadable clips may be slidably carried on the rail member.

In another aspect of the invention, the spreader is comprised of outwardly diverging ramp members between which a positioning recess is formed.

Other aspects of the invention provide one or more of the following features: the clip magazine may comprise a storage enclosure, e.g., a storage handle, through all or part of which the rail member extend;; the rail member may support the spreader in a position disposed outside the storage enclosure or handle.

In another aspect of the invention, the clip applicator includes biasing means mounted on the applicator to urge the spreadable clips from the clip magazine towards the spreader. In still another aspect, the invention provides for a plurality of spreadable clips mounted seriatim within the clip magazine.

Yet another aspect of the invention provides an improvement in a spreadable surgical clip having a tubular body comprising a front face and a pair of opposed leg portions extending from a bight portion and terminating at their distal ends in respective bearing lips facing each other to define therebetween a clamping slit in the front face, and further having an opening formed in the bight portion radially opposite the clamping slit and dimensioned and configured to accept and pass therethrough a wedgeshaped spreader which serves to spread apart the leg portions of the clip. The improvement comprises providing a radially extending slot extending from one bearing lip to the opening to radially bifurcate one of the leg portions of the clip. The invention also provides for an applicator having a plurality of spreadable clips, preferably clips as described herein, carried in the clip magazine of the applicator.

A method aspect of the present invention provides a method of applying surgical clips of the type which are spreadable by application of a spreading force thereto and which close upon release of the spreading force, by means of a manual applicator which includes a spreader having an inlet section and a discharge tip which is wider in the clipspreading direction than the inlet section, the method comprising sliding the clips over the spreader in the direction from the inlet section to the discharge tip whereby to spread the clips on the spreader and discharge the spread clips over the discharge tip and onto tissue to be engaged by the clip.

In another method aspect of the invention, the applicator includes a clip magazine containing a plurality of the clips and the method includes moving the clips seriatim from the clip magazine onto the spreader.

The foregoing and other aspects of the present invention will be apparent from the following disclosure.

BRIEF DESCRIPTION OF THE DRAWINGS

FIG. 7 is a view generally corresponding to that of FIG. 2 showing, part broken away, another embodiment of an applicator in accordance with the present invention;

FIG. 8 is a section view taken along line VIII—VIII of FIG. 7 with the clips omitted for improved clarity of illustration;

FIG. 9 is a section view taken along line IX—IX of FIG. 7;

FIG. 10 is a perspective view of a spreadable clip adapted for the applicator of FIGS. 7-9; and FIG. 11 is a rear view of the spreadable clip of FIG. 10.

DETAILED DESCRIPTION OF THE PREFERRED EMBODIMENTS

The applicator of the invention includes a clip magazine for the storage of a supply of clips and may be provided in a configuration wherein the clip magazine comprises a storage enclosure which may be provided in the forming of a storage handle suitably dimensioned and configured to be comfortably grasped by a surgeon or other operator in the manner illustrated in FIG. 6 of the drawings, as described more fully below. A plurality of spreadable clips is arranged seriatim within the storage enclosure, for example, upon a rail member on which the clips are slidably mounted so that they can be pushed from the rail member over a spreader to open the clips to a spread apart condition in which the clips are pushed off the spreader for application in clamping engagement to a wound or incision. The term "spreadable" clips is used herein and in the claims to refer to clips which can be spread apart for application to tissue and are sufficiently resilient that, upon release of the spreading force, they close at least sufficiently to engage or clamp the tissue to which they are applied.

Figure 1:
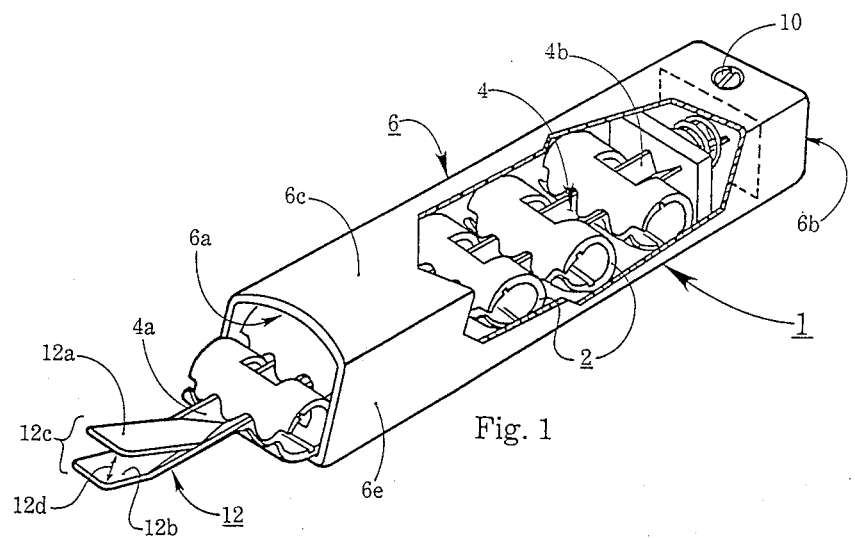
FIG. 1 is a perspective view, with parts broken away and omitted for improved clarity of illustration, of one embodiment of an applicator in accordance with the present invention.
Figure 2:
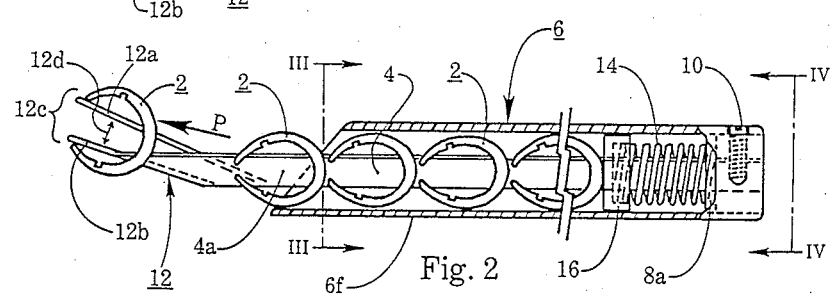
FIG. 2 is a broken section view in side elevation of the applicator FIG. 1.
Figure 3:
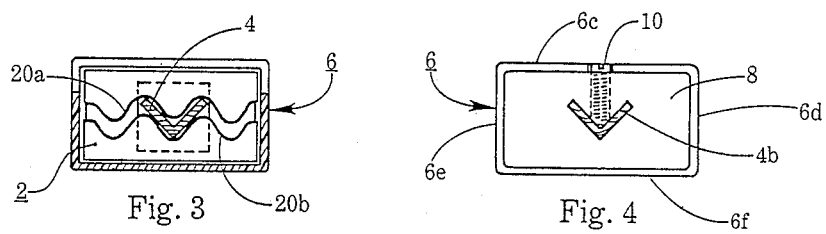
FIG. 3 is a section view taken along line III—III of FIG. 2.
Figure 4:
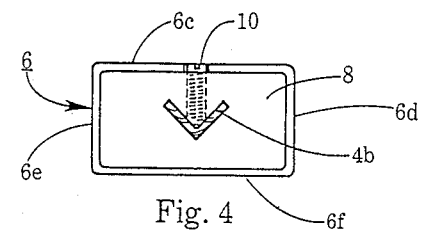
FIG. 4 is an end view taken along line IV—IV of FIG. 2.

Referring now to FIGS. 1-4 there is shown a clip applicator 1 comprising a generally rectangular-shaped storage enclosure which, in the illustrated embodiment, comprises a storage handle 6 having a discharge end 6a and a mounting end 6b. Storage handle 6, which further comprises a top wall 6c, laterally opposite side walls 6d and 6e, and a bottom wall 6f, may be made of any suitable material, such as a metal, e.g., stainless steel, or a plastic, i.e., a synthetic organic polymeric material. A plurality of spreadable clips 2 is mounted seriatim upon a rail member 4 which, as best seen in FIGS. 3 and 4, is V-shaped in cross section. Rail member 4 is cantilever-mounted within storage handle 6 by having the loading end 4b of rail member 4 snugly fitted within a V-shaped groove which extends through a mounting block 8 which closes mounting end 6b of storage handle 6. A set screw 10 is positioned within a threaded bore extending through storage handle 6 and the upper (as viewed in FIG. 4) portion of mounting block 8 in order to engage the loading end 4b of rail member 4 to secure the latter in place within storage handle 6 by means of mounting block 8. Rail member 4 may be provided with a suitable recess in the top thereof for engagement by set screw 10 in order to provide a firm, retaining fit of set screw 10 to rail member 4. Or course, rail member 4 may be mounted within storage handle 6 in any suitable way. For example, rail member 4 could be shrink-fit, friction-fit or otherwise permanently encased within mounting block 8. Thus, mounting block 8 could be made of a plastic material which is molded around the end 4b of rail member 4 which could be of serrated configuration to improve the strength of engagement of mounting block 8 on rail member 4. If end 4b of rail member 4 is permanently affixed within mounting block 8, spreader 12 may be made detachable from rail member 4 for reloading rail member 4 with a fresh supply of clips, or the entire device may be disposable, i.e., designed to be discarded after its supply of clips is used, rather than reloaded. A disposable applicator eliminates the need to re-sterilize the applicator and clips after re-loading the applicator. The disposable applicator and clips will be sterilized by the manufacturer and appropriately sealed to maintain sterility, with the seal being broken only at the point of use.

Regardless of the manner in which rail member 4 is mounted with storage handle 6, as shown in FIGS. 1 and 2, rail member 4 is cantilevered to extend within and through storage handle 6 and extends outwardly of the discharge end 6a thereof and terminates in a free end comprising a discharge section 4a of rail member 4. A spreader 12 is attached to and supported by rail member 4, at the free end, i.e., the discharge section, thereof. As used herein and in the claims, reference to the spreader 12 being "attached" to the rail member includes construction, such as that illustrated, in which rail member 4 and spreader 12 are of integral construction, as well as cases in which spreader 12 is a separate member either permanently or removably affixed to rail member 4. In any case, in the illustrated embodiment, spreader 12 is of generally bifurcated construction being comprised of an upper ramp 12a and a lower ramp 12b. The distal ends of ramps 12a and 12b define the discharge tip 12c of spreader 12 and a positioning recess 12d is formed between ramps 12a and 12b for a purpose described below. The inlet section of the spreader is disposed adjacent to the clip discharge end 6a and, as shown in FIGS. 1 and 2, the discharge tip 12c is wider in the clip-spreading direction than is the inlet section so that the spreader has a wedge-shaped profile which diverges in the clip-spreading direction.

Referring to FIG. 2, a biasing means is provided in the illustrated embodiment by a coil spring 14, one end of which is fixed within a cup-shaped retainer 16 which is slidably mounted on rail member 4. For this purpose, cupshaped retainer 16 has a V-shaped groove formed in the base thereof which groove is dimensioned and configured to snugly but slidably fit over rail member 4. The other end of coil spring 14 is fixed within a collar 8a formed on the inner face of mounting block 8. The biasing means, although useful, is not essential to the device of the invention. The clips may be gravity-fed to the spreader 12 by simply tipping the applicator 1 to point the discharge tip 12c of spreader 12 downwardly. Optionally, a weight may be slidably mounted on rail member 4 behind the last clip, i.e., between the last clip and mounting block 8, to facilitate gravity feed of the clips by preventing one or more of the clips, which are rather light, from jamming and hanging up on rail member 4.

Figure 5:
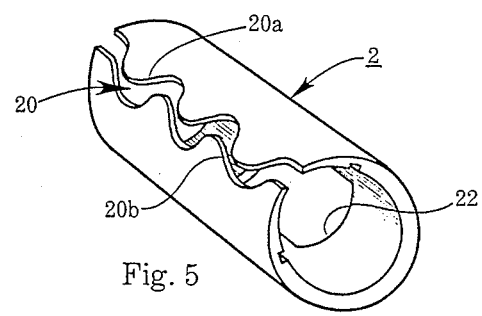
FIG. 5 is a perspective view of a known type of spreadable surgical clip which the applicator of FIG. 1 is adapted to utilize.

FIG. 5 shows a typical spreadable clip 2, which is of generally tubular construction and has formed in its front face portion (unnumbered) a longitudinally extending, tooth-contoured slit 20 extending along its entire longitudinal length and defining opposed bearing lips 20a and 20b. Clip 2 has opposing spreadable leg portions emanating from the rear or bight portion of the clip 2 and terminating in respective bearing lips 20a and 20b which lie on either side of, and cooperate to define therebetween, slit 20. A generally rectangular-shaped opening 22 is formed in the rear or bight portion of the generally cylindrical shaped wall of the clip 2. Opening 22 is located radially opposite and centered on longitudinally extending slit 20. Clip 2 is made of any suitable resilient material, such as a sterilizeable plastic or metal such as, for example, stainless steel. As the clip 2 is made of a resilient material, the leg portions of the clip on opposite sides of slit 20 can be spread apart by applying a spreading or separating force thereto and will come back together to a closed, clamping position upon release of the spreading force. In the illustrated embodiment, the body of the clip 2 is of generally tubular configuration and the bearing lips 20a, 20b are spaced slightly apart when the clip is unstressed, i.e., when the legs of the clip are not spread apart. However, any other suitably designed clips may be used in the applicator of the present invention.

As shown in FIGS. 1, 2 and 3, a plurality of clips 2 is slidably mounted within the storage enclosure provided by storage handle 6. In the illustrated embodiment, the clips 2 are slidably mounted within storage handle 6 by being threaded on a rail member 4 which extends through rectangular-shaped openings 22 (FIG. 5) in the clips 2 and between opposite lips 20a, 20b. (As used herein and in the claims, "threaded" refers to the aforesaid type of thread-through-a-needle arrangement, and should not be confused with utilization of screwthreads.) The toothed contour of lips 20a, 20b cooperate with the V-shaped profile of rail member 4 to help retain clips 2 centered on rail member 4, even when individual clips 2 are outside of storage handle 6, as illustrated in FIGS. 1 and 2.

A plurality of clips 2 may be loaded onto rail member 4 by loosening set screw 10 and withdrawing rail member 4 from storage handle 6 through the discharge end 6a thereof, i.e., leftwardly as viewed in FIG. 2. A plurality of clips 2 is then threaded onto rail member 4 by sliding the clips over the loading end 4b of rail member 4. When the desired number of clips has been loaded so as to substantially fill rail member 4 from discharge section 4a thereof, leaving a suitable length of rail member 4 adjacent loading end 4b thereof clear of clips 2, loading end 4b of rail member 4 is inserted into discharge end 6a of storage handle 6, and moved therein (rightwardly as viewed in FIG. 2) to thread rail member 4 through the V-shaped opening in cupshaped retainer 16, through coil spring 14 and into the V-shaped groove in mounting block 8. Preferably, the interior dimensions of storage handle 6 are sized to slidably engage the top, bottom and opposite side edges of clips 2 so that the clips serve to center rail member 4 and guide it into the V-shaped grooves provided in cup-shaped retainer 16 and mounting block 8. As noted above, rail member 4 preferably has formed in the top thereof adjacent loading end 4b a circular recess (not shown) shaped to receive the bottom end of set screw 10. If set screw 10 is only slightly loosened while rail member 4 is being inserted into storage handle 6, engagement of the recess in rail member 4 by set screw 10 will help to determine when rail member 4 has been pushed the correct distance into storage handle 6. Set screw 10 is then tightened and the clip applicator is ready for use.

Figure 6:
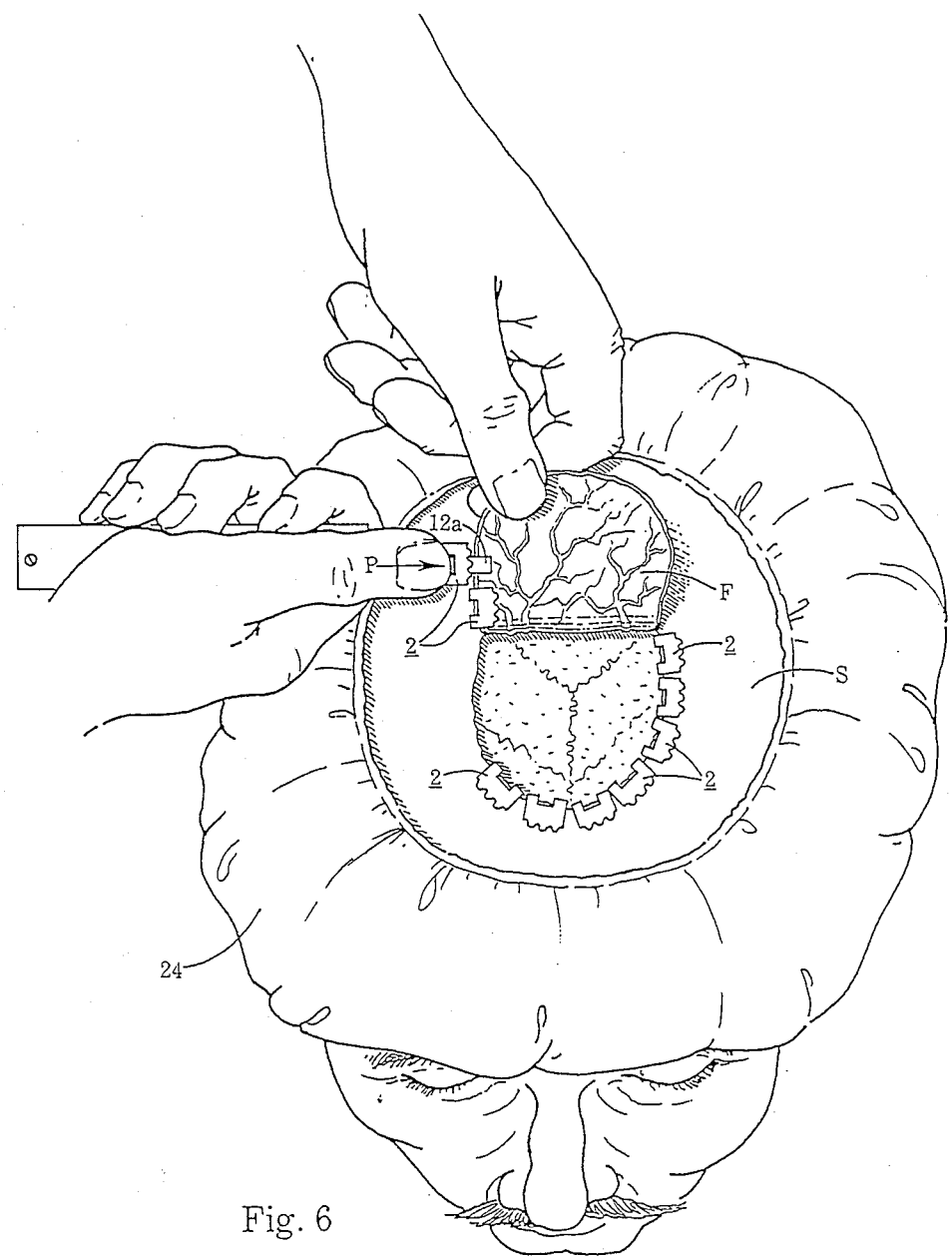
FIG. 6 a perspective view showing tee clamping of a scalp flap-like incision using the applicator of FIGS. 1-4.

FIG. 6 illustrates use of the clip applicator of the invention in cranial surgery and shows the head of a patient wearing a skull covering 24 which has a circular opening (unnumbered) in the top thereof to expose a shaved portion S of the patient's scalp. A U-shaped, generally semi-circular incision has been made in the patient's scalp and the resultant flap F of the scalp has been raised by the surgeon who has applied a series of seven clips 2 along the incision line in the scalp, and is shown in the process of applying a second clip 2 to the periphery of the raised flap F. Additional clips may be placed about the periphery of the flap F and along the remaining unclipped portion of the incision in the scalp for control of bleeding.

In use, storage handle 6 is grasped within the closed palm of the hand with the surgeon's thumb positioned over the top wall 6c thereof, with the tip of the thumb engaging the clip 2 which is positioned exteriorly of storage handle 6. The mode of gripping the clip applicator is shown in FIG. 6, in which most of the applicator is obscured by the surgeon's hand. The lead clip is pushed by the surgeon onto spreader 12 and this results in spreading apart the legs of the lead clip 2 as shown in FIG. 2. With the spread-apart lead clip 2 thus positioned, the surgeon places the applicator adjacent the incision to be clamped together by the clip and pushes the clip in the direction indicated (in FIGS. 2 and 6) by the arrow P over the discharge tip 12c defined by the distal or free ends of ramps 12a and 12b. The positioning recess 12d provided between ramps 12a and 12b is well adapted to receive therein the edge or lip of the wound to be closed or clamped so as to facilitate the ability of the surgeon to precisely position the clip. For example, in FIG. 6 the surgeon is shown applying a clip 2 to the periphery of a flap F incised from a human scalp to clamp the flap F to control bleeding from the edges thereof. Positioning recess 12d admits the edge of flap F between ramps 12a and 12b to provide the surgeon with maneuvering room to selectively position the clip 2 at the edge of the wound. Upon pushing the clip 2 over the discharge tip 12c of spreader 12, the natural resiliency of the clip causes the spread-apart legs to close in clamping engagement upon the incision or wound.

Referring now to FIG. 7 there is shown the discharge end of an applicator in accordance with another embodiment and in which parts corresponding to those of the FIG. 1 embodiment are identically numbered except for the addition of a prime indicator. The spreadable clips illustrated in FIGS. 10 and 11 are generally similar to the clip of FIG. 5 but are slotted, as described below, in order to particularly adapt them to be employed with the applicator of FIG. 7. In the FIG. 7 embodiment, a storage enclosure is provided by storage handle 6' which terminates at discharge end 6a' and, exteriorly of which, a spreader 12' is supported upon a support member comprising, in the illustrated embodiment, a rail member 4'. Spreader 12' is similar in general configuration to spreader 12 of the FIG. 1 embodiment and comprises an upper ramp 12a', a lower ramp 12b', a discharge tip 12c' and a positioning recess 12d'. As best seen by referring to FIGS. 7 and 8 jointly, rail member 4' comprises a vertically positioned, web-like member which extends substantially parallel to the longitudinal axis of storage handle 6'. In the embodiment illustrated in FIG. 7, rail member 4' terminates at approximately the discharge end 6a' of storage handle 6'. However, in an alternate embodiment, rail member 4' could extend through all or most of storage handle 6'. As is the case with the embodiment of FIGS. 1-4, at least part of the support member provided by rail member 4' is disposed between the spreader 12' and the discharge end 6a'. Only a single clip 2' is shown in FIG. 7, for improved clarity of illustration, and it is shown positioned beyond inlet face 18' (FIGS. 7 and 8) of rail member 4'. Rail member 4', including its inlet face 18' and the inlet section of ramp 12', are seen to have a T-shaped cross-section as best seen in FIGS. 8 and 9. As best appreciated with respect to FIG. 9, slit 20' formed between bearing lips 20a and 20b' of clip 2' (FIG. 10) is wide enough to accept inlet face 18' of rail member 4' so that clip 2' can be pushed onto rail member 4' and then spreader 12'. The outward divergence of upper ramp 12a' and lower ramp 12b' serves to spread apart the legs of clip 2'.

As noted above, the clip 2' of FIGS. 10 and 11 is similar in construction to that of FIG. 5, and corresponding parts are identically numbered to those of the FIG. 5 embodiment, except for the addition of a prime indicator. Rectangular opening 22' in the rear or bight portion of clip 2' is dimensioned so as to accept and pass over the widest portion (at discharge tip 12c') of spreader 12'. In order to permit sliding movement over spreader 12' of spreadable clips 2', spreadable clips 2' are provided with a slot 26 which extends radially of the clip from bearing lip 20b' to rectangular opening 22' so that the lower half (as viewed in FIGS. 10 and 11) of clip 2' is bifurcated. The width of slot 26 is sized to accept therein the width of rail member 4' so that clip 2' is "threaded" upon rail member 4'. As noted above, rail member 4' may extend through most or all of storage handle 6' and, when it does, it serves to assist in aligning clips 2' within storage handle 6'. However, as will be appreciated from FIG. 9, the interior of storage handle 6' may be configured and dimensioned so as to slidcase, it may not be necessary to extend rail member 4' throughout the length of storage handle 6, and rail member 4' may be terminated, say at about discharge end 6a' so as to engage each clip 2' just before or as it exits storage handle 6'. Storage handle 6' will guide and align clips 2' until they clear discharge end 6a' at or prior to which time the clips 2' engage rail member 4', which serves to assist in guiding the clips 2' onto spreader 12'.

In addition to the illustrated use of applying hemostatic surgical clips to control bleeding, the applicator of the invention may be used to apply spreadable clips to close a wound or generally, to apply spreadable clips to tissue for any purpose including emergency treatment or any situation in which tissue or other material must be clipped or clamped for any reason. The applicator of the present invention provides rapid application of the clips without the need to load individual clips onto a applicator one at a time. This has obvious advantages, e.g., in reducing the time required for surgical procedures, therefore reducing the time the patient must be kept under anesthesia. In some surgical procedures, as much as twenty minutes may be saved by using the applicator of the present invention instead of prior art devices requiring one-at-a-time loading of clips. The applicator of the present invention is also useable with either the left or right hand, at any angle which the surgeon or operator finds to be convenient.

The applicator of this invention may be used in a number of different applications including applying hemostatic surgical clips to control bleeding, applying spreadable clips to close a wound or incision, or generally to apply spreadable clips for any purpose. Generally, reference to a "surgical" clip is intended to broadly include clips designed to be applied to human or animal or other tissue in surgical, medical, experimental or other procedures.

While the invention has been described in connection with specific preferred embodiments thereof, it will be appreciated upon a reading and understanding of the foregoing that numerous alterations and modifications to the preferred embodiments may be made which nonetheless lie within the scope of the invention and the appended claims.

What is claimed is:

1. A manual applicator for the application of spreadable surgical clips, comprising:

a clip magazine having a clip discharge end and dimensioned and configured to releasably retain within the magazine a plurality of spreadable clips;

a spreader mounted on said clip magazine by a rail member, at least part of the rail member being disposed between the spreader and the discharge end of the magazine to receive spreadable clips from the magazine and carry said clips on the rail member for guided movement of the clips thereon and onto the spreader, the spreader and the rail member each being dimensioned and configured to permit sliding movement thereover of the clips; and biasing means mounted on the applicator to urge the spreadable clips form the clip magazine towards the spreader;

the spreader having an inlet section disposed adjacent to the discharge end of the magazine and a discharge tip which is wider in the clip-spreading direction than its inlet section, thereby providing the spreader with a wedge-shaped profile which diverges in the clip-spreading direction, whereby dislodgement of the spreadable clips from the clip magazine onto the spreader spreads the dislodged clip for ejection of it over the discharge tip of the spreader.

2. The applicator of claim 1 wherein the rail member is cantilevered, thereby having a free end, and the spreader is carried on the free end of the rail member.

3. The applicator of claims 1 or 2 wherein the rail member extends parallel to the longitudinal axis of the applicator.

4. The applicator of claims 1 or 2 wherein the rail member extends at least part way through the clip magazine and carries thereon spreadable clips contained within the clip magazine.

5. The applicator of claim 4 wherein the rail member extends through substantially the entire length of the clip magazine.

6. The applicator of claims 1 or 2 wherein the spreader has outwardly diverging ramp members between which a positioning recess is formed.

7. The applicator of claims 1 or 2 wherein the rail member extends at least part way through the clip magazine.

8. The applicator of claim 7 wherein the rail member has a cross-sectional profile which is dimensioned and configured to be engaged by the spreadable clips so as to slidably retain the clips in oriented, seriatim position on the rail member.

9. The applicator of claim 1 wherein the clip magazine comprises a storage enclosure.

10. The applicator of claim 9 wherein the storage enclosure comprises a storage handle which is dimensioned and configured to be hand held during utilization of the applicator.

11. The applicator of claim 10 wherein at least a portion of the storage enclosure is sufficiently transparent to show the quantity of clips contained therein.

12. The applicator of claim 10 wherein the rail member extends at least part way through the storage handle and supports the spreader outside the storage handle.

13. The applicator of claim 12 wherein the rail member is cantilevered, having one end thereof supported by the storage handle and an opposite, free end which carries the spreader.

14. The applicator of claims 1 or 2 including biasing means carrier on the rail member to urge spreadable clips from the clip magazine towards the spreader and wherein the rail member has spreadable clips slidably mounted thereon.

15. A manual applicator for the application of spreadable surgical clips, comprising:
a clip magazine having a clip discharge end and dimensioned and configured to releasably retain within the magazine a plurality of spreadable clips;
a spreader mounted on said clip magazine by a rail member, at least part of the rail member being disposed between the spreader and the discharge end of the magazine to receive spreadable clips from the magazine and carry said clips on the rail member for guided movement of the clips thereon and onto the spreader, the spreader and the rail member each being dimensioned and configured to permit sliding movement thereover of the clips;
the spreader having an inlet section disposed adjacent to the discharge end of the magazine and a discharge tip which is wider in the clip-spreading direction than its inlet section, thereby providing the spreader with a wedge-shaped profile which diverges in the clip-spreading direction, whereby dislodgement of the spreadable clips from the clip magazine onto the spreader spreads the dislodged clip for ejection of it over the discharge tip of the spreader; and
a plurality of spreadable clips carried within the clip magazine, the spreadable clips respectively having a tubular body comprising a front face and a pair of opposed leg portion extending from a bight portion and terminating at their distal ends in respective bearing lips facing each other to define therebetween a clamping slit in the front face, an opening formed in the bight portion radially opposite the clamping slit and dimensioned and configured to accept and pass the support member and the spreader therethrough, whereby to spread apart the leg portions for the clip.

16. The applicator of claim 15 wherein the rail member of the applicator is a cantilevered rail member and the clips are slidably mounted upon the rail member which passes through the rectangular opening and the clamping slit of respective clips.

17. The applicator of claim 15 wherein respective ones of the clips have a radially extending slot extending from one bearing lip to the rectangular opening to radially bifurcate one of the leg portions of the clip.

18. The applicator of claim 17 wherein the respective radially extending slots of the clips are aligned with the rail member and dimensioned and configured to accept the rail member slidably therein.

19. The applicator of claim 18 wherein the clips are slidably mounted upon the rail member, which passes through the radially extending slots of the clips.

20. The applicator of claims 1 or 2 wherein the rail member extends at least part way through the clip magazine, and including a plurality of spreadable clips carried on the rail member within the clip magazine.

21. A manual applicator for the application of spreadable surgical clips, comprising:
a clip magazine comprising a storage handle having mounted therein a rail member which is dimensioned and configured to slidably receive a plurality of spreadable surgical clips thereon, and upon which is supported a spreader having an inlet section facing the storage handle and a discharge tip at its end opposite its inlet section, the spreader being wider in the clip-spreading direction at its discharge tip than at its inlet section so as to have a wedge-shaped profile in the clip-spreading direction; whereby dislodgement of the spreadable surgical clips from the rail member onto the spreader spreads the dislodged clip on the spreader, from which the spread clip may be ejected over the discharge tip thereof, the applicator including biasing means mounted thereon to urge the spreadable clips from the rail member towards the spreader.

22. The applicator of claim 21 including a plurality of spreadable clips carried within the clip magazine thereof.

23. The applicator of claim 21 wherein the plurality of spreadable clips are mounted seriatim on the rail member.

* * * * *